(12) United States Patent
Dmuschewsky

(10) Patent No.: US 9,724,117 B2
(45) Date of Patent: Aug. 8, 2017

(54) MEDICAL, IN PARTICULAR SURGICAL, SLIDING-SHAFT INSTRUMENT

(71) Applicant: Waldemar Link GmbH & Co. KG, Hamburg (DE)

(72) Inventor: Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 363 days.

(21) Appl. No.: 14/425,440

(22) PCT Filed: Aug. 28, 2013

(86) PCT No.: PCT/EP2013/067842
§ 371 (c)(1),
(2) Date: Mar. 3, 2015

(87) PCT Pub. No.: WO2014/037266
PCT Pub. Date: Mar. 13, 2014

(65) Prior Publication Data
US 2015/0209060 A1 Jul. 30, 2015

(30) Foreign Application Priority Data
Sep. 4, 2012 (EP) .................................... 12183021

(51) Int. Cl.
*A61B 17/29* (2006.01)
*A61B 17/16* (2006.01)
(Continued)

(52) U.S. Cl.
CPC ...... *A61B 17/2909* (2013.01); *A61B 17/1608* (2013.01); *A61B 17/00234* (2013.01);
(Continued)

(58) Field of Classification Search
CPC .......... A61B 17/1608; A61B 17/00234; A61B 17/29; A61B 2017/2916; A61B 2017/292;
(Continued)

(56) References Cited

U.S. PATENT DOCUMENTS

2006/0116706 A1 6/2006 Martin
2011/0046661 A1\* 2/2011 Kuehn ............... A61B 17/1608
606/206

FOREIGN PATENT DOCUMENTS

DE 43 16 769 5/1994
DE 297 18 969 3/1998
(Continued)

*Primary Examiner* — Todd J Scherbel
*Assistant Examiner* — George J. Ulsh
(74) *Attorney, Agent, or Firm* — Sand & Sebolt

(57) ABSTRACT

A medical sliding-shaft instrument having a first handle arm, a second handle arm pivotably mounted to the first handle arm, a shaft connected to the first handle arm and a slider coupleable to the second handle arm and axially displaceable on the shaft. The slider is removable from the shaft and is guided along a sliding path. A cross-pin couples the second handle arm to the slider and is received in a slot defined by first and second legs of the second handle arm. The first leg is a resilient tongue moveable transversely to a longitudinal axis of the first leg and outwardly away from the second leg. The second handle arm is positioned so that the cross pin lies in the slot. The cross pin is covered and held back by the first leg and is released by applying a force and displacing the end of the first leg.

13 Claims, 5 Drawing Sheets

(51) Int. Cl.
  *A61B 17/00* (2006.01)
  *A61B 90/00* (2016.01)
(52) U.S. Cl.
  CPC ......... *A61B 17/29* (2013.01); *A61B 2017/292* (2013.01); *A61B 2017/2902* (2013.01); *A61B 2017/2916* (2013.01); *A61B 2017/2917* (2013.01); *A61B 2017/2924* (2013.01); *A61B 2017/2944* (2013.01); *A61B 2017/2947* (2013.01); *A61B 2090/0813* (2016.02)
(58) Field of Classification Search
  CPC .... A61B 2090/0813; A61B 2017/2902; A61B 2017/2909; A61B 2017/2924; A61B 2017/2944; A61B 2017/2947; B25B 7/00; B25B 7/12
  USPC ........................................................ 606/207
  See application file for complete search history.

(56) References Cited

FOREIGN PATENT DOCUMENTS

| | | |
|---|---|---|
| DE | 197 48 369 | 5/1999 |
| DE | 100 61 512 | 6/2002 |
| DE | 20 2008 001 675 | 4/2008 |
| DE | 20 2009 002433 | 4/2009 |
| DE | 20 2012 001 348 | 5/2012 |

\* cited by examiner

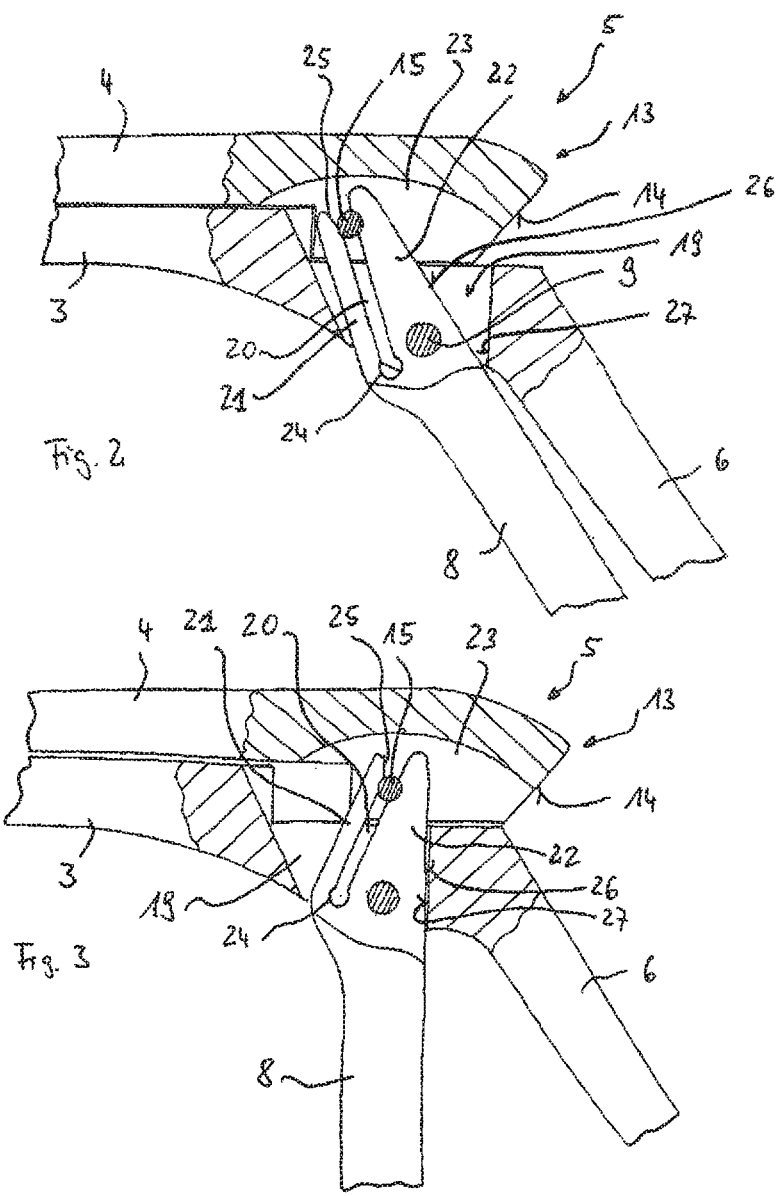

MEDICAL, IN PARTICULAR SURGICAL, SLIDING-SHAFT INSTRUMENT

TECHNICAL FIELD

The present invention relates to a medical, in particular surgical, sliding-shaft instrument having a first handle arm and a second handle arm pivotably mounted with respect to the first handle arm, having a shaft element connected to the first handle arm and a slider that is axially displaceable on the shaft element and can be coupled to the second handle arm, wherein the slider can be removed from the shaft element in a retracted proximal end position of its sliding path and in the proximal end position of additional regions of its sliding path displaced in the direction of a pushed-forward distal end position, is guided inseparably on the shaft element, and wherein a cross in arranged on the slider is accommodated in a first slot of the first handle arm, which is open at the end and is bordered by two legs for coupling the second handle arm to the slider.

PRIOR ART

Such sliding-shaft instruments are characterized in that they have a typically elongated shaft element on which a slider is arranged displaceably in the axial direction of the shaft element. The slider and shaft element are typically connected to one another by a guide, which does not allow separation of these two elements over a wide range of possible positions of the slider and shaft element relative to one another, and which guides the longitudinal movement of the slider and securing it with respect to additional relative movements of the slider relative to the shaft element. Such guides may be implemented, for example, by means of wedge pieces engaging in a dovetail groove on one of the elements or a wedge piece on the other one of the aforementioned elements.

Furthermore, such sliding-shaft instruments comprise a first handle arm and a second handle arm, wherein the second handle arm is mounted pivotably with respect to the first handle arm. The mounting may be directly on the first handle arm, but also on one other of the parts and/or elements of the sliding-shaft instrument, for example, on the shaft element. What is important is only that pivoting of the two handle arms relative to one another is possible. The handle arms, which are also frequently referred to as "handle branches" in this technical field, are handle pieces for handling the sliding-shaft device, which at the same time also fulfill a lever arm function. They may be designed to be comparable, for example, to the handle arms of scissors instruments or the like.

The sliding-shaft instruments, which are in general the subject matter of the invention described herein, typically have a function section on a distal end of the shaft element, which function section also includes, in its functionality, the distal end of the slider, which is axially displaceable on the shaft element. Thus, for example, the distal end of the shaft element and the distal end of the slider may be designed to form two punching jaws of a punch. Blades may be provided, which make the sliding-shaft instrument into a cutting instrument and/or air nippers or pincers. Corresponding handle elements may be arranged on the distal ends to make a gripper out of the sliding-shaft element, etc. It is basically possible here to consider all possible embodiments of an instrument, which can be operated by means of a sliding-shaft technique and which presupposes the use of a lengthened shaft in an advantageous manner in particular and/or offers advantages for use by means of such a shaft. Typically, such sliding-shaft instruments are used in the field of minimally invasive procedures, for example, to permit access to regions inside the body access by introduction through natural body orifices, for example, for clearing out paranasal sinuses or removing polyps through the nostrils or also surgical procedures in the region of the abdomen through small access openings and incisions or procedures in the region of the spine from the abdominal side through a minimally invasive access of small dimensions. However, additional application options are also conceivable, for example, as holders for swabs or the like as part of "traditional" procedures and operations, where it is advantageous not to cover the actual working area in which the swab is to be used, by holders of large dimensions and thereby restrict the view and therefore to arrange corresponding devices such as swabs on the end of long and narrow instrument shafts.

For a cleaning and disinfection that is necessary after use of such sliding-shaft instruments, the latter in most cases are designed to be dismantleable. This then creates a possibility of releasing the slider—typically in a proximal end position—from the shaft element and removing it. Thus, in this proximal end position, the lock between the slider and the shaft element to prevent displacement across the relative direction of axial movement is eliminated. In addition, in such an end position, a possibility of releasing the slider from a coupling with the second handle arm is to be created.

Comparable sliding-shaft instruments are disclosed, for example, in DE 197 48 369 A1. In the instrument disclosed there, a twistable lock element, which, in the release position, allows a further movement of the slider beyond the proximal end position, is arranged on the first handle arm, wherein the cross pin is then allowed [to move] out of the slot formed in the second handle arm.

Another comparable sliding-shaft instrument is disclosed and described in DE 20 2008 001 675 U1. In a comparable design solution, a locking element is also provided on the first handle arm, stopping the slider in a proximal end position, permitting, on its release, a further axial longitudinal movement of the slider in the proximal direction relative to the shaft element. In such a further movement, a guide nose on the slider is moved into a position in a corresponding guide groove on the shaft element, in which it can be separated from the shaft element, while the cross pin also slides on the slider out of the slot in the second handle arm.

DE 100 61 512 A1discloses a comparable sliding-shaft instrument with which a locking lever also stops the slider in a proximal end position when the locking lever is in a blocking position. When the locking lever is moved out of the blocking position and into a release position, a movement of the slider beyond the proximal end position, relative to the shaft element and up to a position in which the cross pin can be removed from the guide slot is made possible. A spring-loaded locking ball, which is arranged in a leg bordering the slot in the second handle arm, forms a certain latch engagement of the cross pin in the slot, which can be overcome when a releasing force is exceeded.

In another sliding-shaft instrument, which is disclosed in DE 297 18 969 U1, the proximal end position of the slider is formed by a spring and path bordering rod formed with a rod element, which is connected to one of the handle arms and detachably connected to one another. If the releasable connection between the rod elements is disconnected, the slider can be moved further in the proximal direction and the cross pin can be released from the slot for separating the elements for a dismantling of same.

It has now been found that the previously known designs and mechanisms for the releasable connection of the shaft element, slider and handle arm components are awkward to handle, which relates to operation, on the one hand, and the cleaning and sterilization, on the other hand. First, in the case of the locking switches arranged in the region of the handle arms, there is the risk of unintentional operation during use, in particular when the locking switches are designed as sliding switches, for example, when an additional pressure must be applied by the thumb on a hand operating the sliding-shaft instrument in an upper section of the instrument on the proximal end of the shaft element and/or in the upper region of a handle arm. If a movement of the slider in the direction of the proximal end is then carried out and it goes beyond the end position, in which the slider and shaft element are still connected, the instrument may then be dismantled unintentionally during use with corresponding negative consequences and impairment of the sequence of the medical procedure in which the sliding-shaft instrument is used. Furthermore, all such locking switches, bolt slides or turn bolts offer additional small interspaces, into which impurities can penetrate together with blood, tissue fragments, bone chips or the like during the medical procedure and use of the sliding-shaft instrument, which interspaces are naturally difficult to access and can therefore be cleaned only with substantial effort, and often even only inadequately, and then sterilized.

The object of the present invention is to create a simplification here and to specify a generic sliding-shaft instrument, which is easy to handle and can be cleaned well, without leaving residues, and is easy to sterilize.

DESCRIPTION OF THE INVENTION

According to the invention, the object is achieved by designing a medical, in particular surgical, sliding-shaft instrument of the aforementioned type, so that a first leg of the legs bordering the first slot is formed as a resilient tongue that is movable outward away from the second one of the legs, across its direction of longitudinal extent, wherein the second handle arm is positioned in the proximal end position in such a way that the cross pin lies in the first slot and is at least partially covered and retained by the first leg, formed as a resilient tongue, in a release direction which points essentially perpendicular to the axial line of the shaft element in the direction of the slider, which cross pin is releasable by applying a releasing force in the release direction and displacement of the end of the first leg, directed against the spring force of the resilient tongue, and wherein a lug is arranged on the proximal end of the slider, protruding in the proximal end position beyond a proximal end of the shaft element, and by means of which a releasing force acting in the direction of release can be applied to the slider.

In the embodiment as described above, an important element is first that the first slot is bordered, not by rigid legs, for example, but instead the first leg, at least this leg, is designed to be movable as a resilient tongue in the transverse direction. This embodiment makes it possible to achieve a locking of the individual parts of the sliding-shaft instrument that can be dismantled without, for example, having to use additional auxiliary means, such as locking slides or other locking elements, which, in particular, also raise the aforementioned problems in the cleaning and sterilization to be performed after use of the sliding-shaft instrument, in addition to possible operating errors. The particular arrangement and position of the elements of the cross pin and of the first slot relative to one another in the proximal end position is also important and relevant to the invention. This arrangement namely also secures the slider and holds it in the assembled state of the sliding-shaft instrument, namely retaining it by the first leg of the first slot and its spring force. Only when such a spring force is overcome, can the first leg be pressed outward, the first slot being spread, so that the cross pin is forced out of the first slot in the proximal end position, and the slider, which does not have any further connection to the shaft element in this proximal end position, can be raised and released from the remaining elements. Firstly, it is advantageously not necessary to put the slider in a release position beyond the proximal end position in the direction of the proximal adjustment path, as required by some of the sliding-shaft instruments according to the prior art. Furthermore, the particular arrangement and geometric coordination of the elements of the first leg, the first slot and the cross pin are of relevance. In other words, in the proximal end position, the cross pin must be shifted so far in the direction of the open end of the first slot that, although it is still at least partially covered by the first leg bordering the first slot, this is true only to the extent that this first leg can be pushed aside with a releasing force, which is directed against the restoring force of the resilient tongue forming the first leg, so that the path for the cross pin out of the open end of the first slot is free. To apply such a releasing force without using an additional tool, the lug according to the invention is provided. This may be formed, for example, on an extension which protrudes beyond the proximal end of the shaft element in the proximal end position of the slider and/or is formed on such a projection. Likewise, laterally protruding regions or only one such region may form a corresponding lug. A rear extension, protruding beyond the proximal end of the shaft element in the proximal end position of the slider, has the advantage that it can be operated easily using the thumb of one hand operating this element in handling of the sliding-shaft instrument according to the invention. Thus a simple one-handed dismantleability can be achieved, wherein the operator's second hand is free, in order, for example, to grip the slider thereby released and to set it down.

The first slot advantageously has a V-shaped or wedge-shaped widened area on its open end. This is designed in particular so that, when the slider is placed on the shaft element in joining the sliding-shaft instrument in the proximal end position of the slider, its region in which the cross pin is arranged is inserted into this V-shaped or wedge-shaped widened area, the cross pin spreads this first leg, widening the first slot by applying a compressive force and overcoming the spring force of the first leg formed as a resilient tongue, and enters the deeper region of the slot until the first leg springs back into its normal position, i.e., the cross pin engages in and/or snaps into the position that is held.

To greatly reduce the risk of cracking at the base of the slot of the first slot in a deflection of the first leg, designed as a resilient tongue, i.e., a load of the spring thereby formed, it may be provided according to an advantageous refinement of the invention that a widening of the slot is provided at the base of the first slot between the legs and may have a cross section in the form of a segment of a circle in particular. The larger the radius of such a slot-widening area designed in the form of a circle, the smaller is the risk of cracking at this location.

It is fundamentally possible that the second leg is also a leg formed as a resilient tongue. However, in an advantageous embodiment of the invention, it is preferred that this leg is a rigid leg. In particular with such a rigid leg, a greater force may be applied to the cross pin guided in the first slot, so that this second rigid leg is advantageously the leg, which, when operated in a direction of movement of a clamping or cutting operation, causes a transfer of force to the cross pin.

On the whole, in a preferred embodiment of the invention, the legs bordering the first slot act in such a way that the second leg transfers to the cross pin a force for moving the slider in the direction of the distal end position when the handle arms are operated in a first operating direction, while the first leg transfers to the cross pin a force for moving the slider in the direction of the proximal end position when the handle arms are operated in a second operating direction. Thus, in this implementation, a higher force is to be expected, in particular in the movement of the slider in the direction of the distal end position because this is a punching direction, a cutting direction or a clamping direction for gripping tools, for example.

In the sliding-shaft instrument according to an advantageous embodiment of the invention, a finger recess is shaped in the surface of the second handle arm on its side facing the first handle arm. This finger recess forms a defined abutment for the index finger of the operator's hand, for example, when a releasing force is applied to the lug with another finger, in particular the thumb. In other words, it is a design which makes it more ergonomic and user friendly.

In particular, although this is not absolutely necessary, a finger loop may also be formed on the free ends of the handle arms. When operating the sliding-shaft instrument, the thumb and index finger, for example, or the thumb and middle finger of the operator's hand that operates the instrument can be inserted, for example, so that corresponding operating forces are transferred easily and reliably to the handle arms in both a first operating direction, in which the two handle arms are moved toward one another, and also in a second operating direction, in which the handle arms are moved away from one another and are spread.

For a further improved cleaning after use of the sliding-shaft instrument, it is advantageous if, according to another advantageous refinement of the invention, it is provided that the second handle arm is releasably connected to the first handle arm and/or to the shaft element. This releasable connection can be secured, in particular, by connecting the slider to the shaft element and securing the slider to the cross pin in the first slot in the second handle arm, so that, after releasing the slider from the shaft element and the second handle arm, the latter can be released easily from the first handle arm and/or the shaft element. To do so, the second handle arm may comprise, for example, a pivot pin having one free end, the pivot pin being inserted at its free end into a corresponding pivot bearing receptacle on the leg element and/or the first handle arm, and being removable therefrom accordingly to release the second handle arm.

A preferred embodiment of the sliding-shaft instrument according to the invention can be seen in scissors and/or a tong-like cutting and/or pincer instrument. Here, a first stationary blade may be formed on the distal end of the shaft element, and furthermore, a second blade that is movable relative to the first blade may also be arranged there, coupled to the slider in such a manner that during a displacement of the slider in the axial direction, the blades move toward and/or away from one another. However, the sliding-shaft instrument according to the invention may naturally also be implemented in other tool variants, for example, as a punch, as a gripper or a similar tool, as previously mentioned in the introduction to the general description.

According to another advantageous and possible embodiment of the sliding-shaft instrument according to the invention, the latter may have a second slot that is open at one end in the region in which the first slot is arranged in the second handle arm, this second slot extending between the first leg and a third leg. The first leg moves toward the third leg at the same time when the first leg moves outward away from the second leg and across its direction of longitudinal extent, wherein the third leg forms a stop, limiting the path of movement of the first leg. Such an embodiment helps to prevent the first leg, which is designed as a resilient tongue, from being deflected to an excessive extent in a deflection due to an operation of releasing or connecting the slider to/from the shaft element and threatening to break and/or develop cracking at the base of the slot. A corresponding deflection of the slot, designed as a resilient tongue, too far is prevented by the third leg, which forms a stop. The second slot, with its slot width, limits the path of movement of the first leg in its deflection.

The second slot, which is provided in the possible embodiment referred to above, may advantageously run parallel to the first slot and may extend essentially over the same length into the material of the second handle arm. This parallel slot guide and extent over essentially the same length into the material of the second handle arm yields, in particular, a first leg designed as a resilient tongue and having a uniform material thickness and an attachment point situated at the same level on both sides (determined by the base of the slot of the adjacent first and/or second slot(s)). In this embodiment, the third leg may advantageously also be a rigid leg, i.e., without any resilient effect. It is thus also ensured in particular that this leg, which forms the stop, will not also yield resiliently in an excessive application of force, but instead will remain rigid and "unavoidable" as a stop.

Inasmuch as reference is made in general in the preceding description to a "first slot," which is essential for the invention and must be provided from a structural standpoint, this does not mean, for example, that a sliding-shaft instrument according to the invention must have more than approximately just one slot, namely the first slot in any possible embodiment. The term "first slot" was introduced merely for better differentiation in comparison with the "second slot," which is designed as described above and is provided in a special exemplary embodiment.

In another embodiment variant, the longitudinal slot may have a circular widened area in a region near its free open end, the diameter of this widened area corresponding to the diameter of the cross pin. The cross pin can engage in such a widened area, thereby predefining certain longitudinal positions of the slide on the shaft element as "catch positions," engaging the sliding-shaft instrument in such positions.

BRIEF DESCRIPTION OF THE DRAWINGS

Additional advantages and features of the invention are derived from the following description of possible exemplary embodiments of the invention on the basis of the accompanying figures, in which:

FIG. 2 shows, in an enlarged and partially cut-away diagram, a detail of the sliding-shaft instrument according to FIG. 1, with the slider situated in the distal end position, and in a design according to a first exemplary embodiment;

FIG. 3 shows an enlarged and partially cut-away detail of the first exemplary embodiment, comparable to that in FIG. 2, having the slider in the proximal end position;

METHOD(S) OF IMPLEMENTING THE INVENTION

Figure 1:
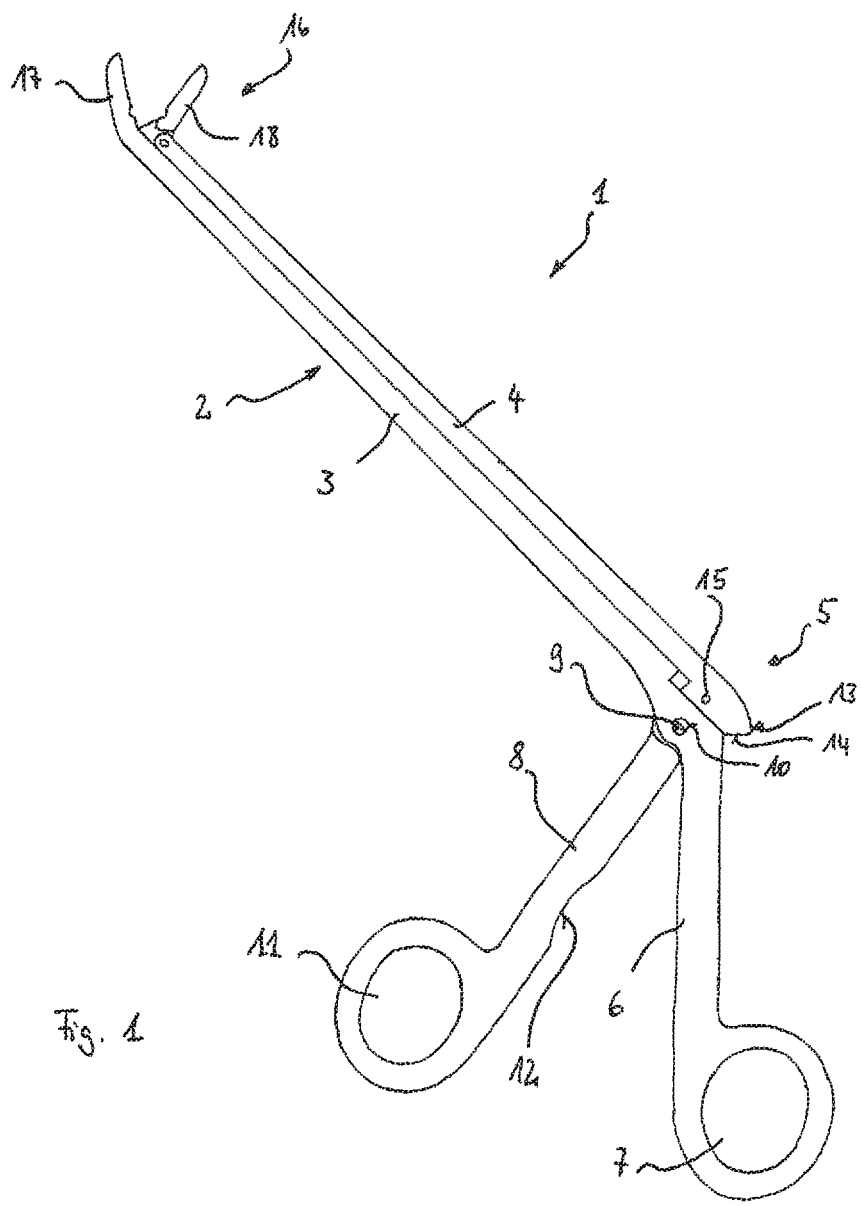
FIG. 1 shows a schematic view of a first one of a sliding-shaft instrument according to the invention, having a slider situated in the proximal end position.

The figures show, in two possible exemplary embodiments, a sliding-shaft instrument according to the invention schematically and explained below—in both design variants. The figures are mere schematic diagrams and are by no means drawn to scale or complete in all details. As already mentioned, they serve only to illustrate the possible implementation of the essential features of the sliding-shaft instrument according to the invention in an illustrative exemplary embodiment. The figures show the same and/or similar elements, labeled with the same reference numerals, also for the different exemplary embodiments.

FIG. 1 shows a sliding-shaft instrument 1 according to the invention, in the form of a so-called rongeur in this embodiment variant. This sliding-shaft instrument 1 has an elongated straight shaft 2, which contains a shaft element 3 and a slider 4, which is movable relative to this shaft element 3 in the axial direction of the shaft 2 and/or of the shaft element 3. On a proximal end 5, a first handle arm 6 is permanently connected to the shaft element 3, in particular in one piece, and is angled with respect to the longitudinal direction and/or the axial direction of the shaft element 3, with a first handle arm 6 being integrally molded thereon. This first handle arm 6 has a finger loop 7 on its free end.

A second handle arm 8 is arranged pivotably relative to the first handle arm 6. In addition, it is supported with a pivot bearing pin 9 in a pin receptacle 10 formed as a borehole in the transitional area between the shaft element 3 and the first handle arm 6. The second handle arm 8 also has a finger loop labeled as 11 on its free end. In addition, a finger recess 12 is shaped in the surface of the second handle arm 8 on a side facing the first handle arm 6. This finger recess serves to support an index finger or middle finger on the operating hand when a spreading movement of the handle arms 6, 8 is carried out using the thumb of the operator's hand in the finger loop 7, or the slider 4 is released from the shaft element 3 and the second handle arm 8 in a manner to be described later.

It can also be seen that in its proximal end position shown in FIG. 1, the slider 4 has an extension 13 that protrudes beyond the proximal end of the shaft element 3 and/or beyond the shape of the first handle arm 6 on its rear and/or proximal end, having a lug 14 designed as an acting surface. This lug 14 and its meaning are explained in greater detail below on the basis of the description of FIG. 3 in particular.

Also apparent is a cross pin 15 arranged on the slider 4, recognizable here with an end face and/or front face penetrating through the surface of the slider.

On its distal end 16, the sliding-shaft instrument 1 has two reaming blades 17 and 18, which jointly form a cutting tool. The first reaming blade 17 is permanently connected in one piece to the shaft element 3 and angled with respect to the latter. The second cutting blade 18 is connected to the shaft element 3 in a pivot bearing and is also hinge-connected to the slider 4. In this way, a closing and/or opening movement of the cutting blades 17 and 18 is achieved by a longitudinal axial movement of the slider 4 along the shaft element 3. If the slider 4 is moved along the distal end 16, the cutting blades 17 and 18 close and can sever bone or cartilage material. In the opposite direction of movement of the slider 4, the cutting blades 17, 18 open.

The axial movement of the slider 4 in the direction of the distal end 16 is caused by contraction of the two handle arms 6 and 8. By means of a connection of the second handle arm 8 to the cross pin 15, and thus also to the slider 4 yet to be described in greater detail on the basis of the following figures, a movement of the slider 4 in the axial direction, pointing in the direction of the distal end 16, is induced along the shaft element 3. A movement of the slider 4 in the direction of the proximal end 5 is achieved by the spreading of the handle arms 6, 8 by means of the same entraining mechanism.

A guide formed between the shaft element 3 and the slider 4 may be implemented, in particular, by a dovetail groove, which runs in the axial direction and is created on the side of the shaft element 3 facing the slider 4 and also by a similarly shaped sliding block on the surface of the slider facing the shaft element 3. This guide is designed so that it is separable in the proximal end position of the slider 4, shown in FIG. 1, i.e., for example, the sliding block can be removed from the dovetail groove by a corresponding widening of the groove. These elements are not shown here but they can be seen in the diagram of the second exemplary embodiment of the invention in FIGS. 4 to 8. This guide may also be designed like the guides described and disclosed in DE 20 2008 001 675 U1 or like that in DE 20 2012 001 348 U1.

In a first exemplary embodiment, additional details of the movement transfer mimics and, at the same time, the releasable connection between the second handle arm 8 and the slider 4 are also shown in the partially sectional detail diagrams in FIGS. 2 and 3. FIG. 2 shows a situation in which the slider 4 is in its distal end position. in FIG. 3, the slider 4 is in its proximal end position. In the following description, unless the respective figure is mentioned explicitly, reference is being made to both figures at the same time.

It can be seen there how one end of the second handle 8 arm is guided through a bushing 19 formed in the transition region between the shaft element 3 and the first handle arm 6, wherein the pivot bearing pin 9 is arranged in the bushing 19 and a pivot axis that is stationary relative to the first handle arm 6 and the shaft element 3 is defined. Also apparent here is a slot 20 formed on the end of the second handle arm 8 opposite the handle loop 11 (not shown in the figures). The cross pin 15 is held in this slot 20, which is bordered at the sides by a first leg 21 and a second leg 22, so that an articulated connection between the second handle arm 8 and the slider 4 is formed by means of this arrangement. To provide space for this articulated connection, a recess having an arc-shaped cross section and/or a clearance 23 is/are formed on the proximal end 5 in the slider 4. The first leg 21 is formed as a resilient tongue due to a smaller material thickness and therefore is also outwardly movable relative to the second leg 22 against a restoring force, which forces this leg 21 back into its resting position. To reduce, ideally eliminate, the risk of cracking at the base of the slot 20 when the leg 21 is deflected, the slot 20 is provided with a slot widening area 24 having a cross section in the form of a segment of a circle.

In contrast to the first leg 21, the second leg 22 is rigidly shaped and is not bendable.

At its open end, a wedge-shaped widened area of the slot is achieved by a bevel 25 on the free end of the first leg 21. The bevel is shaped in such a manner that with a position of the slider 4 in its proximal end position, as shown in FIG. 3, the course of the bevel 25 is essentially perpendicular to the direction of extent of the shaft element 3.

During a closing and/or spreading movement of the two handle arms 6, 8, the cross pin 15 now moves back and forth in the slot 20 and is entrained, so that it results in an axial longitudinal movement of the slider 4 relative to the shaft element 3. For a movement in the direction of the distal end 16, the force is transferred from the second handle arm 8 to the cross pin 15 by way of the rigid leg 22, so that a greater force must be transmitted here. Since this direction of movement of the slider 4 determines the closing movement of the clearing blades 17 and 18, a considerable measure of force may therefore be transferred in a cutting operation. In the opposite direction, the opening direction, the force required for the movement of the slider 4 in the direction of the proximal end 5 is transferred to the cross pin 15 via the first leg 21 designed as a resilient tongue. A lower force is typically required in the opening movement of the reaming blades 17, 18, so that no malfunction occurs here that could occur due to an outwardly directed yielding motion by the first leg 21 which takes place against the spring force.

In the position shown in FIG. 3, in which the slider 4 is in its proximal end position, it can be seen that the first leg 21 protrudes beyond the cross pin 15 at one end in a direction perpendicular to the direction of longitudinal extent of the shaft element 3 and secures it in its position. However, if a compressive force is transferred to the lug 14, for example, using the thumb of the operator's hand, this leads to a yielding movement of this first leg 21, outwardly directed and acting against the spring force of the first leg 21, which is designed as a resilient tongue, until the cross pin 15 is released. Then the slider 4 can be lifted off the shaft element 3 and removed.

The slider 4 is then optionally also connected to the shaft element 3 by means of the reaming blade 18, which, however, poses no problems for the cleaning of these elements. If necessary a corresponding separation on the distal end 16 is also possible for the purpose of cleaning, in which case the mechanisms and steps in this regard may be carried out in manner known per se, depending on the design of the tool.

In the position shown in FIG. 3, in which the slider has reached its proximal end position, the second handle arm 8 is in contact with an inside surface 26 on a stop surface 27 adjacent to the bushing 19, so that a continued upward movement of the slider 4 in the direction of the proximal end is impossible, even when applying a releasing force to the lug 14, until the cross pin 15 has been released from the slot 20.

To assemble the sliding-shaft instrument 1 according to the invention, the second handle arm 8 is guided into the position shown in FIG. 3, which is defined by the stop on the inside surface 26 of the handle arm 8 and the stop surface 27, and the slider 4 is guided in the direction of the shaft element 3, so that the cross pin 15 is guided past the bevel 25 on the first leg 21 in the slot 20 and is engaged by applying a compressive force with spreading of the first leg 21 in this slot. After the connected position has been reached, a transfer of force in the direction of the distal end can be exerted by closing the handle arms 6 and 8.

In both releasing the slider 4 from the shaft element 3 and in connecting it thereto, the longitudinal guide, which is described in greater detail with respect to the same embodiment according to FIGS. 4 through 8, with regard to the longitudinal guide, but differing in the connection of the second handle arm 8 to the cross pin 15 is released or connected, respectively.

FIGS. 4 through 8 show a second design variant of the link between the second handle part 8 and the slider 4 in a sliding-shaft instrument 1 according to FIG. 1, which is described in greater detail below.

The fundamental design of the sliding-shaft instrument 1 in this second exemplary embodiment is the same as that already described with respect to the first exemplary embodiment, and including FIGS. 1 through 3. In this respect, reference can and is made to the previous description with regard to the design of the sliding-shaft instrument 1 and the function of the individual elements. This is true in particular where the same reference numerals are used for the same elements in FIGS. 4 through 8, as also shown in FIGS. 1 through 3.

The essential difference between the second exemplary embodiment shown in FIGS. 4 through 8 and the first exemplary embodiment already described above lies in the design of the upper connecting end of the second handle part 8, which establishes the connection to the slider 4 by means of the cross pin 15. As is clearly seen in FIGS. 4 and 5 in particular, a longitudinal slot 20 is also provided in this exemplary embodiment at the connecting end of the handle part 8; the cross pin 15 rests in this longitudinal slot and a force is transferred from the second handle part 8 to the slider 4 for its longitudinally guided movement along the shaft element 3 by means of this longitudinal slot. In this exemplary embodiment as well, the slot 20 is bordered by a first leg 21 and a second leg 22. Here, too, the first leg 21 is designed as a resilient tongue with a bevel 25 on its free end, permitting easier insertion of the cross pin 15 into the slot 20, as already described above on the basis of the exemplary embodiment described previously. In this embodiment variant as well, the second leg 22 is a rigid leg, which does not yield in a resilient manner even when a force is exerted on the cross pin 15 by means of this leg to move the slider 4 along the shaft element 3 in the direction of the distal end.

In deviation from the design in the first exemplary embodiment, the handle part 8 also has a second slot 29 on its upper end, which is connected to the side of the first leg 21 opposite the first slot 20 and is bordered on the other side of the slot by a third leg 28. The slots 20 and 29 in this case run essentially in parallel, resulting in an essentially uniform material thickness in this direction between these first upright legs 21. Furthermore, both slots 20 and 29 are inserted and/or cut to equal depths in the material of the free end of the handle part 8, so that they yield a link at the same level on both sides, between the lower end of the first leg 21 and the material of the handle part 8 below it.

The third leg 28 is again a rigid leg, i.e., a leg, which does not undergo deformation or yield in a resilient manner with a force applied to it in the usual handling of the sliding-shaft instrument 1.

Figure 4:
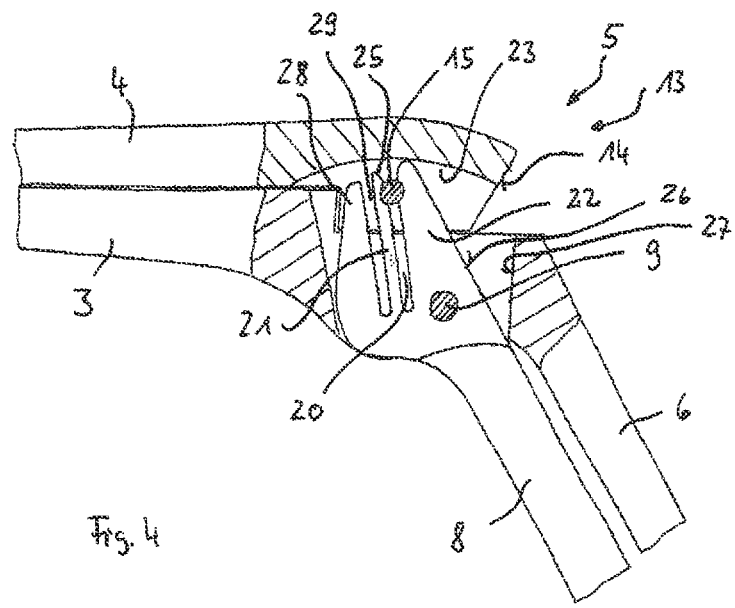
FIG. 4 shows a diagram comparable to that in FIG. 2 and a partially cut-away a detail of the sliding-shaft instrument according to FIG. 1, with the slider situated in the distal end position and in a design according to a second exemplary embodiment.
Figure 5:
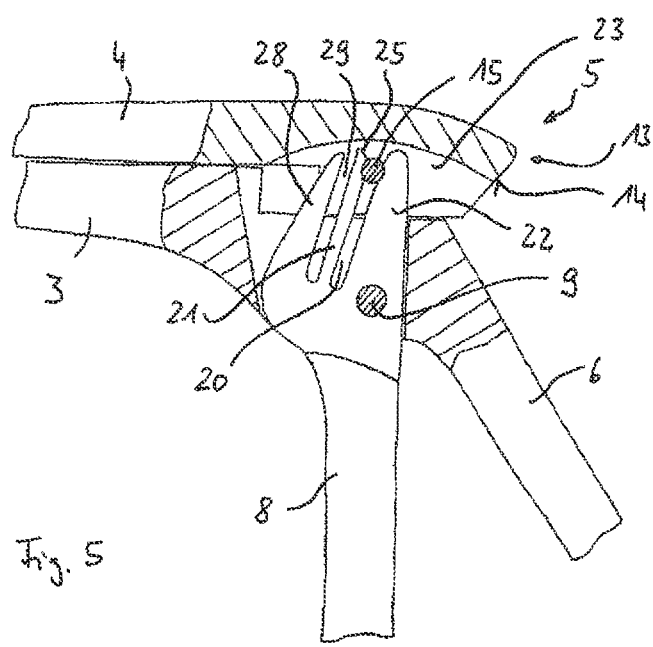
FIG. 5 shows an enlarged and partially cut-away detail of the second exemplary embodiment, comparable to that in FIG. 3, with the slider in the proximal end position.

FIGS. 4 and 5 show first (FIG. 4) the detail of the sliding-shaft instrument according to the second exemplary embodiment, with a position of the slider 4 on the shaft element 3 in a position shifted maximally in the direction of the distal end, and in the opposite direction in FIG. 5, in a position of the slider 4 shifted to the maximal extent in the direction of the proximal end 5. In this regard, these FIGS. 4 and 5 are the same in their positions and representations as FIGS. 2 and 3, so that here the differences between the exemplary embodiments are particularly apparent.

Figure 6:
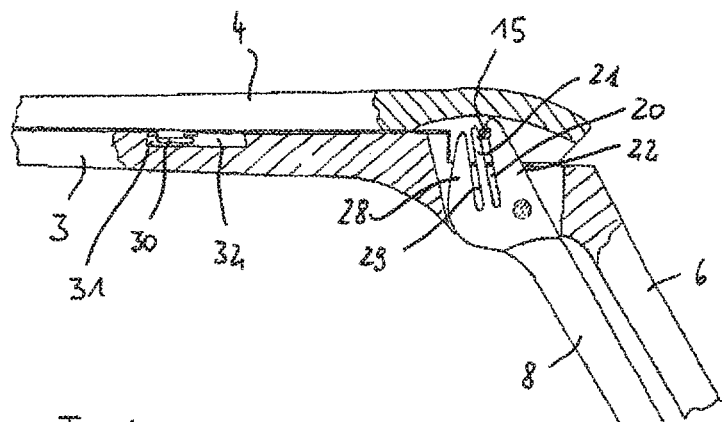
FIG. 6 shows a larger detail of the sliding-shaft instrument in the design of the second exemplary embodiment with the slider in the proximal end position, in which a guide connection between the slider and shaft element can also be seen.
Figure 7:
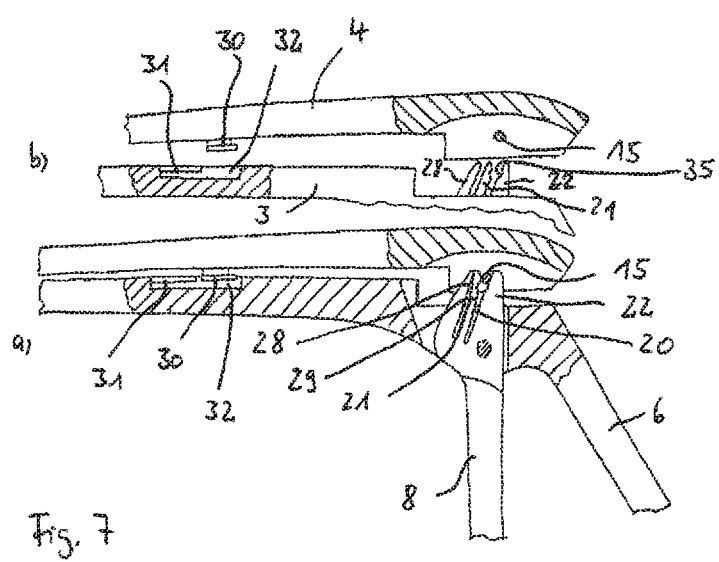
FIG. 7 shows, in two diagrams a) and b), the situation when separating the slider from the shaft element in the second exemplary embodiment, including the separation of the guide connection.
Figure 8:
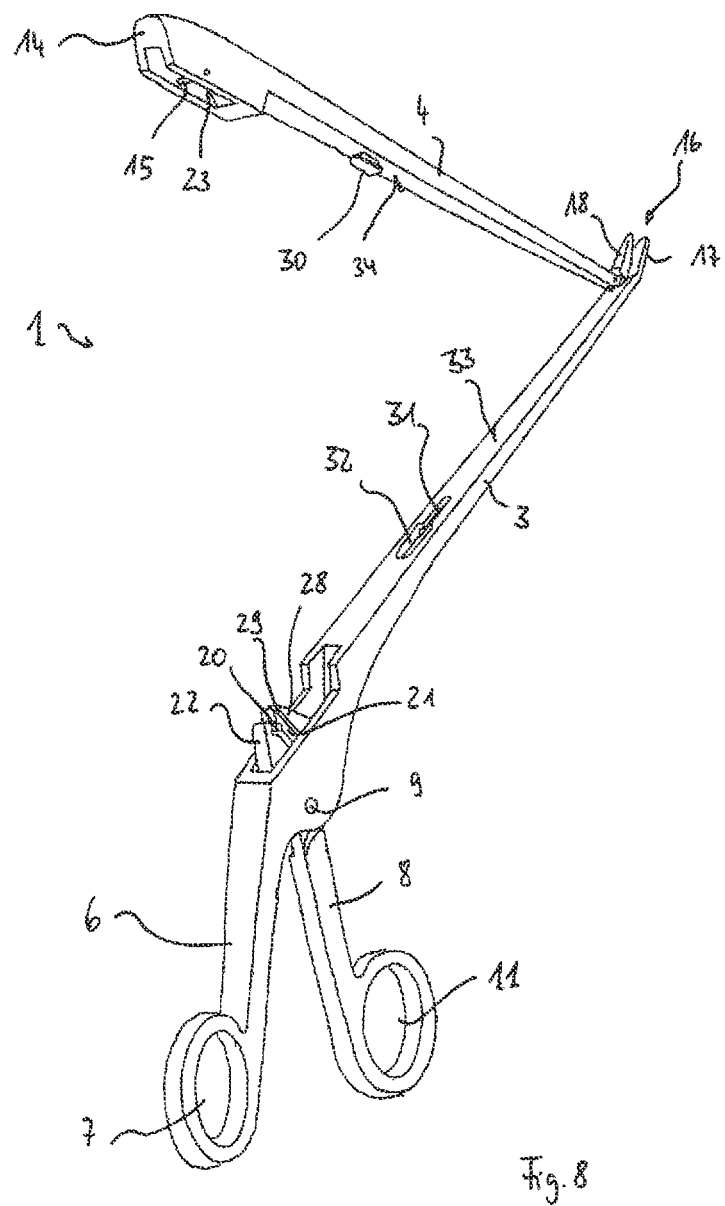
FIG. 8 shows a three-dimensional view of the sliding-shaft instrument according to the second exemplary embodiment with the slider raised from the shaft instrument.

In addition, the diagrams in FIGS. 6 through 8 show the structures that ensure a longitudinal guidance of the slider 4 on the shaft element 3, and at the same time retain the connection across this longitudinal direction. These structures, which are represented explicitly in conjunction with the diagram of the sliding-shaft instrument 1 according to the second exemplary embodiment and are described in greater detail below, are also similarly present in the first exemplary embodiment according to FIGS. 1 to 3 and are designed on the individual elements in this way. In this regard, the following description may also be used for the first exemplary embodiment described above because it also applies equally to the latter.

it can be seen that a guide groove 31 running in the longitudinal direction of the shaft element 3 is arranged on the surface 33 facing the slider 4 when the sliding-shaft instrument 1 is assembled. The guide groove 31 has a groove base, which is widened relative to the slot near the surface, thereby resulting in laterally protruding guide and restraint webs. On its proximal end, the guide groove is provided with a widened area 32 of the groove, in which the protruding guide webs have been cleared out, the width of the slot has been adapted to the width of the base of the groove and thus widened.

In addition, a sliding block 30, which protrudes away from this surface 33 of the shaft element 3 is integrally molded on a surface 34 of the slider 4, which is facing the surface 33 of the shaft element 3 in the assembled state of the sliding-shaft instrument 1. This sliding block has a narrow connecting web to the surface 34 and has a widened base at the side. The width of the base of the sliding block 30 is dimensioned in such a way that the sliding block 30 can be inserted into the widened area 32 of the groove. If the slider 4 is then advanced further in the direction of the distal end, the base of the sliding block 30 slides along the base of the groove and the web moves into the slot of the guide groove 31. The sliding block 30 is then retained in the guide groove 31 because of the interaction of the guide and restraint webs with the base of the sliding block 30, where it is retained against any separating movements across the longitudinal extent of the slider 4 and the shaft element 3.

The situation of insertion and/or separation of the sliding block 30 into or out of the groove-widened area 32 and/or guide groove 31 is illustrated in the diagrams a and b in FIG. 7, where it can be easily seen how the sliding block 30 (cf. FIG. 7a) fits in the groove-widened area and can be inserted there. FIG. 7b shows the situation after the separation of the elements, i.e., the slider 4 and the shaft element 3, and/or shortly before assembling them.

FIG. 7 also contains an illustration of how the third leg 28 functions; on insertion of the cross pin 15 into the slot 20, i.e., in a situation in which the first leg 21, which is designed as a resilient tongue, is moved away from the second leg 22 with widening of the slot 20, in particular on its free end, this leg forms a stop for the free end of the first leg 21. In the situation illustrated in FIG. 7a, the free end of the first leg abuts the free end of the third leg 28, so that no further yielding of the first leg 21 is possible. This prevents overspreading of the slot 20, so that there is no risk of damage to the first leg 21 or cracking at the base of the slot 20. It is also clearly apparent that in the yielding of the first leg 21, formed as a resilient tongue, to open the slot 20, the width of the additional slot 29 is reduced and is closed completely when the first leg 21 comes to a stop against the third leg 28.

In the second exemplary embodiment shown, the first slot 20 has a circular widened area 35 that is adjusted in radius approximately to the diameter of the cross pin 15 in an upper section. This widened area forms a type of retention trough and serves to define a resting position of the cross pin 15, in which the pin rests after being inserted into the slot 20 and, depending on the material properties of the legs 21, 22, may optionally engage there. In particular when the cross pin 15 migrates in the slot 20 in the direction of the base of the slot, i.e., in the direction of the free end of the handle section 8 during the movement of the slider 4 in the direction of the distal end to close the two reaming blades 17 and 18, this will take place in the exemplary embodiment shown again with opening of the slot 20, i.e., with a resilient yielding of the first leg 21. Thus, in the distal end position, the sliding-shaft instrument 1 is constructed so that the cross pin again rests in the circular widened area 35 and is restrained there by the spring action of the first leg 21, which is designed as a resilient tongue. In this way, two positions are formed, in which the sliding-shaft instrument 1 is secured in a certain manner and can also engage there, depending on the design of the legs 21, 22, namely in the distal end position, in which the reaming blades 17, 18 are closed, and in a proximal end position, in which the reaming blades 17, 18 are open, and the slider can be released by applying a compressive force to the pressure surface 14 as described in detail above using as an the example the first exemplary embodiment, and as also to be practiced for the second exemplary embodiment. These additional restraining positions are additionally secured by this restraining mechanism in a particularly favorable manner because with the slider 4 held in the distal end position, the reaming blades 17, 18 remain closed, thus supported with organic material to be removed with the sliding-shaft instrument 1, additionally secured by this retaining mechanism, without a surgeon having to hold the sliding-shaft instrument in the distal position with a higher application of force that would otherwise be necessary when extracting the sliding-shaft instrument from the working area, in order not to release the organic material that is to be removed on its path through the body, for example, and thereby lose it.

Such a circular widened area 35 as that depicted in the second exemplary embodiment is also provided for the first exemplary embodiment.

It has also become clear again, from the preceding description of the exemplary embodiments, which advantages are offered by the design of the novel sliding-shaft instrument according to the invention, by, in particular, being able to omit locking mechanisms and corresponding parts. This not only facilitates operation of the sliding-shaft instrument during use as well as in dismantling and/or assembling but also facilitates cleaning and sterilization.

LIST OF REFERENCE NUMERALS

1 Sliding-shaft instrument
2 Shaft

3 Shaft element
4 Slider
5 Proximal end
6 First handle arm
7 Finger loop
8 Second handle arm
9 Pivot bearing pin
10 Pin receptacle
11 Finger loop
12 Finger recess
13 Extension
14 Lug
15 Cross pin
16 Distal end
17 Reaming blade
18 Reaming blade
19 Bushing
20 Slot
21 First leg
22 Second leg
23 Recess
24 Widened area of slot
25 Bevel
26 Inside surface
27 Stop surface
28 Third leg
29 Slot
30 Sliding block
31 Guide groove
32 Widened area of groove
33 Surface
34 Surface
35 Circular widened area

The invention claimed is:

1. A medical sliding-shaft instrument comprising:
a first handle arm;
a second handle arm pivotably mounted with respect to the first handle arm;
a shaft element connected to the first handle arm;
a slider that is axially displaceable on the shaft element and is configured to be coupled to the second handle arm, wherein the slider is removable from the shaft element in a retracted proximal end position of the slider's sliding path and in the proximal end position of additional regions of the slider's sliding path is displaced in the direction of a pushed-forward distal end position and wherein the slider is guided inseparably on the shaft element;
a cross pin arranged on the slider is accommodated in a first slot of the first handle arm, wherein the first slot is open at the end and is bordered by two legs configured to couple the second handle arm to the slider, wherein a first leg of the two legs bordering the first slot is formed as a resilient tongue that is movable outwardly and away from a second leg of the two legs across the first leg's longitudinal extent;
wherein the second handle arm is positioned in the proximal end position so that the cross pin lies in the first slot and is at least partially covered and retained by the first leg, formed as the resilient tongue in a release direction, which is generally perpendicular from an axial line of the shaft element in the direction of the slider, and the cross pin is releasable from the slot by applying a releasing force in the release direction with displacement of an end of the first leg out of the slot, directed against a spring force of the resilient tongue, and wherein a lug is arranged on the proximal end of the slider, wherein the lug is protruding in the proximal end position beyond a proximal end of the shaft element and is configured to be applied to the slider when the releasing force in the release direction is applied.

2. The sliding-shaft instrument according to claim 1, further comprising a V-shaped or wedge-shaped widened area at an open end of the first slot.

3. The sliding-shaft instrument according to claim 1, further comprising a slot-widened area in the form of a circular segment formed at a base of the first slot between the two legs.

4. The sliding-shaft instrument according to claim 1, wherein the second leg is a rigid leg.

5. The sliding-shaft instrument according to claim 1, wherein, on activation of the first and second handle arms into a first operating direction, the second leg transfers a force for moving the slider in the direction of the distal end position to the cross pin, wherein the first leg transfers a force to the cross pin for moving the slider in the direction of the proximal end position, and wherein the first leg applies a force to the cross pin in operation of the first and second handle arms in a second direction of operation.

6. The sliding-shaft instrument according to claim 1, wherein a finger recess is shaped into a surface of the second handle arm on a side facing the first handle arm.

7. The sliding-shaft instrument according to claim 1, wherein a finger loop is formed on a free end of each of the first and second handle arms.

8. The sliding-shaft instrument according to claim 1, wherein the second handle arm is releasably connected to the first handle arm or the shaft element.

9. The sliding-shaft instrument according to claim 1, wherein a first stationary blade is formed on the distal end of the shaft element, and furthermore, a second blade movable relative to the first blade is also arranged there, is coupled to the slider in such a way that with a displacement of the slider in the axial direction, the blades move toward or away from one another.

10. The sliding-shaft instrument according to claim 1, further comprising a second slot, which is open at the end in the region of the first slot extending between the first leg and a third leg, wherein the first leg, when it is moved outward away from the second leg across its direction of longitudinal extent, is at the same time moving toward the third leg, and the third leg forms a stop, limiting the path of movement of the first leg.

11. The sliding-shaft instrument according to claim 10, wherein the second slot runs parallel to the first slot and extends essentially over the same length into the material of the second handle arm as the first slot.

12. The sliding-shaft instrument according to claim 10, wherein the third leg is a rigid leg.

13. The sliding-shaft instrument according to claim 1, wherein the longitudinal slot, in a region near the slot's free open end, has a circular widened area whose diameter corresponds to a diameter of the cross pin.

* * * * *